United States Patent [19]

Jones et al.

[11] Patent Number: 4,628,935
[45] Date of Patent: Dec. 16, 1986

[54] DEFIBRILLATOR ADAPTED FOR USE WITH ACCESSORY CASSETTES

[75] Inventors: Paul W. Jones, Issaquah; Rodney J. Merry; Douglas T. Hakala, both of Bothell, all of Wash.

[73] Assignee: Physio-Control Corporation, Redmond, Wash.

[21] Appl. No.: 689,746

[22] Filed: Jan. 8, 1985

[51] Int. Cl.[4] .............................................. A61N 1/36
[52] U.S. Cl. ................................................ 128/419 D
[58] Field of Search ........................... 128/419 D, 783

[56] References Cited

U.S. PATENT DOCUMENTS

| | | | |
|---|---|---|---|
| 3,747,605 | 7/1973 | Cook | 128/419 D |
| 3,798,542 | 3/1974 | Dempsey | 128/419 D |
| 3,865,101 | 2/1975 | Saper et al. | 128/419 D |
| 4,097,113 | 6/1978 | McKelvy | 128/419 D |
| 4,419,998 | 12/1983 | Heath | 128/783 |

Primary Examiner—William E. Kamm
Attorney, Agent, or Firm—Christensen, O'Connor, Johnson & Kindness

[57] ABSTRACT

A defibrillator adapted for use with accessory cassettes. In one embodiment, the defibrillator comprises a body, a pair of electrodes, means for mounting the electrodes to the body, means for mounting an accessory device to the body, and contact means for electrically connecting the electrode elements to the accessory device when the electrodes and accessory device are mounted to the body. The defibrillator may also include a test load, and the contact means may be adapted to electrically connect the test load to the electrode elements when the accessory device is not mounted to the body and to break the electrical connection between the test load and the electrode elements when the accessory device is mounted to the body. In one embodiment, the accessory device comprises an adapter for connecting an accessory electrode set to the defibrillator.

4 Claims, 5 Drawing Figures

DEFIBRILLATOR ADAPTED FOR USE WITH ACCESSORY CASSETTES

FIELD OF THE INVENTION

The present invention relates to defibrillators and, in particular, to a defibrillator that is adapted for use with accessory cassettes.

BACKGROUND OF THE INVENTION

A defibrillator is a therapeutic instrument that is useful in curing certain cardiac irregularities, particular ventricular fibrillation and atrial fibrillation. The defibrillator typically includes a pair of large paddle electrodes, and operates to apply a high energy DC pulse to a patient through the paddle electrodes when appropriately triggered by an operator. The paddle electrodes are held in the operator's hands when the defibrillation pulse is administered. In one common technique (anterior/anterior), one paddle electrode is placed lateral to the upper sternum and below the right clavicle on the patient's right chest, and the second paddle electrode is placed on the patient's lower left chest, usually just below and lateral to the cardiac apex. In a second known arrangement (anterior/posterior), the anterior paddle electrode is placed over the precordium, and the posterior paddle electrode is placed on the patient's back behind the heart. Since a patient will usually be unconscious and lying on his or her back, the size of a paddle electrode and the requirement that it be held by the operator generally make the anterior/posterior technique impractical when only paddle electrodes are available.

Other well known types of defibrillator electrodes include internal electrodes and low-profile disposable electrodes. Internal electrodes are small electrodes that are used during surgery when the heat is exposed, and are applied directly to the heart. Disposable electrodes are flat, low-profile electrodes that include adhesive so that the electrode can be secured to a patient's skin. Unlike a paddle electrode, a disposable electrode can be applied to a patient's back, permitting the use of the somewhat more efficient anterior/posterior defibrillation technique. The use of disposable electrodes also permits the electrodes to remain attached to a patient while the patient is moved, e.g., while the patient is moved from an ambulance into an emergency room, thereby permitting a faster response should defibrillation subsequently be needed.

In the past, defibrillators have accommodated different types of electrodes by providing a set of external connectors to which the different electrodes could be electrically connected. The disadvantage of such an arrangement is that the paddle electrodes are not always available for use. Furthermore, such an arrangement gives rise to the possibility that the defibrillator will be left in a state in which no electrodes are attached or available.

SUMMARY OF THE INVENTION

The present invention provides a defibrillator adapted for use with an accessory device such as an accessory cassette adapter for connecting an accessory electrode set to a defibrillator.

In one embodiment, the defibrillator comprises a body, a pair of electrodes, means for mounting the electrodes to the body, connector means for mounting an accessory device to the body, and contact means. Each electrode includes an electrode element adapted for application to a patient and through which a defibrillation shock may be delivered to the patient. The contact means electrically connects the electrode elements to the accessory device when the accessory device is mounted to the body. The defibrillator may further comprise a test load, and the contact means may be adapted to electrically connect the test load to the electrode elements when the accessory device is not mounted to the body and to break the electrical connection between the test load and the electrodes when the accessory device is mounted to the body. The accessory device may comprise an adapter for connecting accessory electrodes to the defibrillator, or a pacemaker.

DETAILED DESCRIPTION OF THE INVENTION

Figure 1:
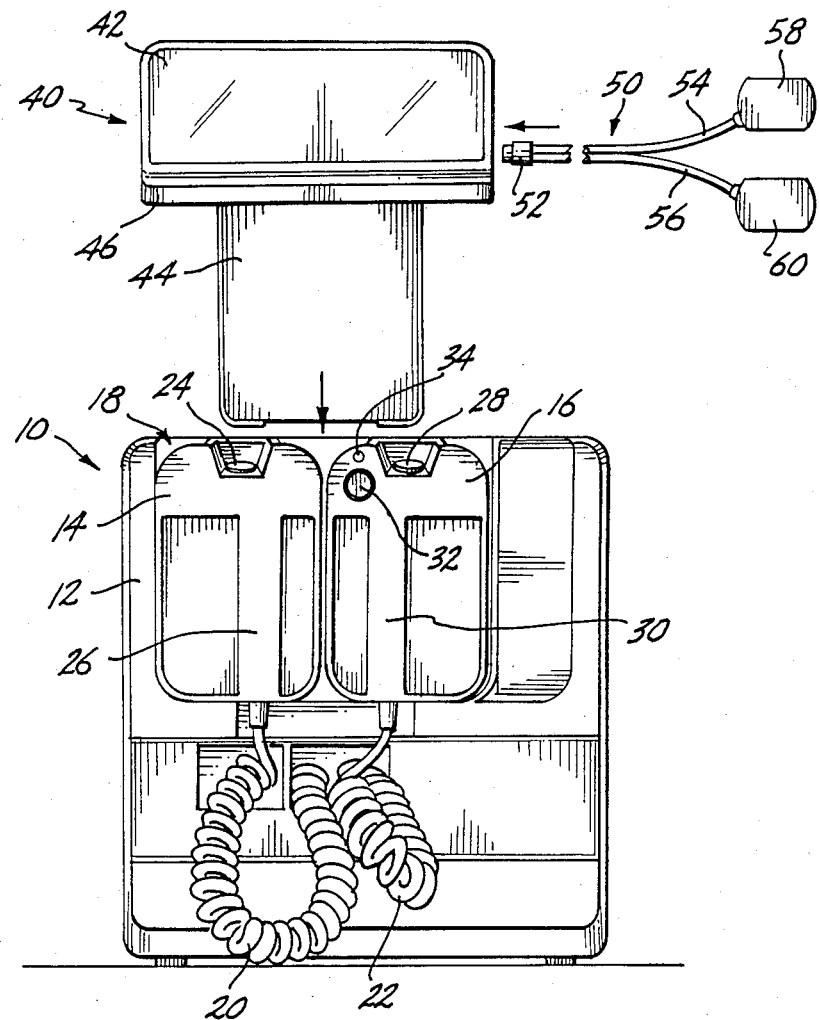
FIG. 1 is a front elevational view of a defibrillator, accessory cassette and electrode set.

FIG. 1 illustrates defibrillator 10 that is adapted to receive cassette 40. Defibrillator 10 comprises body 12 and paddle electrodes 14 and 16. The upper, front portion of body 12 is shaped to form recess 18, recess 18 being dimensioned to receive paddle electrodes 14 and 16 for stowing the paddle electrodes when they are not in use. Paddle electrodes 14 and 16 are electrically connected to defibrillator 10 by means of cables 20 and 22 respectively. Paddle electrode 14 includes discharge switch 24 and handle 26. Paddle electrode 16 includes discharge switch 28, handle 30, charge switch 32 and charge indicator 34. To use the paddle electrodes to apply a defibrillation shock to a patient, the operator depresses charge switch 32 to initiate charging of the defibrillator's energy storage means. While the energy storage means is charging, charge indicator 34 blinks on and off. When the energy storage means is fully charged, charge indicator 34 blinks steadily on. The operator may then grip paddle electrodes 14 and 16 by means of handles 26 and 30 respectively, remove the paddle electrodes from recess 18, and then deliver a defibrillation shock by applying the paddle electrodes to a patient and simultaneously depressing discharge switches 24 and 28.

Figure 2:
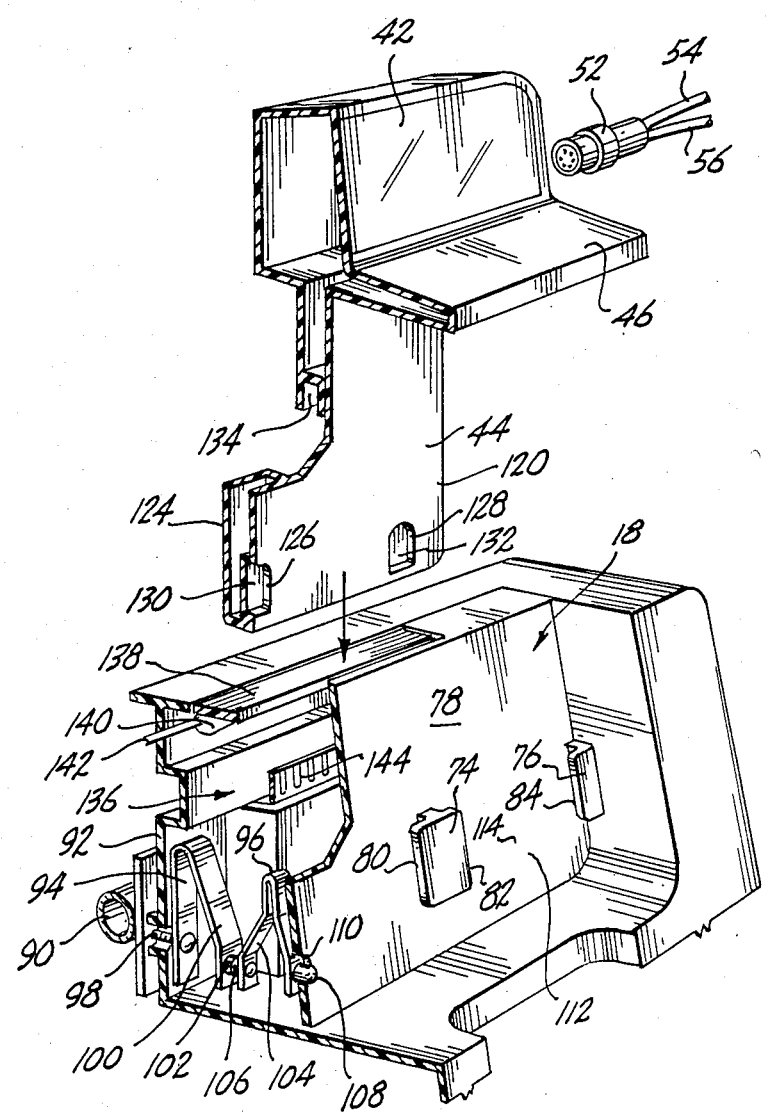
FIG. 2 is a cut away perspective view showing a portion of the defibrillator, accessory cassette and electrode set.

The defibrillator of the present invention is adapted to receive cassette 40 that may be used to connect additional electrodes to the defibrillator, or for other purposes as described below. Cassette 40 comprises housing 42 depending tongue 44, and forwardly extending guard 46 (FIG. 2). In the embodiment of FIG. 1, cassette 40 is adapted to receive a set of disposable electrodes illustrated schematically by electrode set 50. Electrode set 50 comprises connector 52, cables 54 and 56, and disposable electrodes 58 and 60. Connector 52 plugs into a matching connector 53 (FIG. 4) in the side of body 42 of cassette 40. Tongue 44 is adapted to be received in a recess in housing 12 immediately behind recess 18. As described below, electric current for disposable electrodes 58 and 60 is supplied through paddle electrodes 14 and 16. Thus the use of disposable electrodes does not require disconnection of the paddle electrodes, and the paddle electrodes are always available for use.

Figure 3:
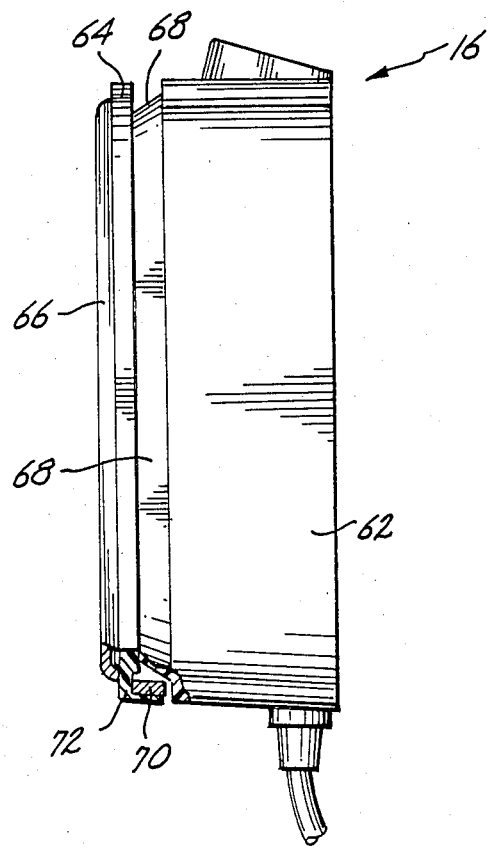
FIG. 3 is a side elevational view of one paddle electrode.

Referring now to FIGS. 2 and 3, paddle electrode 16 comprises body 62, retainer plate 64 underlying the body, and electrode element 66 underlying the retainer plate. Electrode element 66 is the conductor through which electrical energy flows to the patient. The portion of body 62 immediately above retainer plate 64 is indented to form recess 68 that extends around the entire periphery of paddle electrode 16. At the lower end of the paddle electrode, magnet 70 is mounted in recess 68 by means of flange 72 that extends upward from the lower edge of retainer plate 64. The purpose of magnet 70 is described below. When electrode 16 is stowed in recess 18, the paddle electrode is secured against lateral motion by central guide 74 and edge guide 76. Central guide 74 and edge guide 76 extend outward from partition 78 that forms the rear wall of recess 18. Central guide 74 extends in a forward direction from partition 78, and includes lateral projections 80 and 82 that are parallel to but spaced from the forward surface of partition 78. Edge guide 76 extends outwardly from partition 78, and includes projection 84 that is also parallel to but spaced from the outer surface of partition 78. Paddle electrode 16 is stowed in recess 18 by sliding the paddle electrode downward, with electrode element 66 abutting partition 78, such that the lateral edges of retainer plate 64 slide under projections 82 and 84, and such that the projections are received within recess 68 of the paddle electrode. A second edge guide (not shown) is positioned to the left of central guide 74, and paddle electrode 14 is stowed between such other edge guide and central guide 74 in a manner similar to that described for paddle electrode 16.

Defibrillator 10 includes test load 90 that may be used to test the operation of the defibrillator. Such a test is performed by charging the defibrillator's energy storage means, and then discharging the energy storage means through the test load via paddle electrodes 14 and 16. As is well known to those skilled in the art, the results of such a test can be monitored by the defibrillator and can be used to confirm that the defibrillator is in good working order. Test load 90 is mounted to partition 92 that is positioned within the defibrillator a short distance behind partition 78.

Paddle electrode 14 may be electrically connected to test load 90 by means of conductors 94 and 96 positioned between partitions 78 and 92. Conductor 94 is electrically connected to test load 90 by means of bolt 98 that passes through partition 92 and that also serves to support conductor 94 and test load 90. The forward part of conductor 94 includes spring arm 100 that has electrical contact 102 mounted in a forward facing direction at its lower end. Conductor 96 is mounted to the rear surface of partition 78, and includes rearwardly extending spring arm 104 that includes rearwardly facing contact 106 at its lower end. Conductor 96 also includes contact 108 that extends through opening 110 in partition 78. The spring force of spring arms 100 and 104 are sufficient to maintain contacts 102 and 106 in electrical contact with one another. When paddle electrode 14 is stowed in recess 18, the electrode element of the paddle electrode makes electrical contact with contact 108, thereby establishing an electrical connection between paddle electrode 14 and test load 90. A similar arrangement of conductors (not shown) is provided in order to connect paddle electrode 16, when stowed in recess 18, to the other end of test load 90. FIG. 2 illustrates contact 112 that extends through opening 114 in partition 78 and that is adapted to make contact with electrode element 66 of paddle electrode 16 when the paddle electrode is stowed in recess 18.

As illustrated in FIG. 2, tongue 44 of cassette 40 is a hollow member that comprises forward surface 120 and rear surface 124. Forward surface 120 includes openings 126 and 128 behind which electrical contacts 130 and 132 respectively are positioned. Tongue 44 further comprises edge connector socket 134 that faces downward into a channel formed in the lower portion of rear surface 124. Appropriate conductors (not shown) extend upward from electrical contacts 130 and 132 and from edge connector socket 134 to connector 53 in housing 42. Tongue 44 is adapted to be inserted in cavity 136 that is formed between partitions 78 and 92. The top of cavity 136 is closed by door 138 that is pivotally mounted by hinges 140 to rod 142. Door 138 is biased by springs (not shown) into the closed position indicated in FIG. 2. The interior of cavity 136 includes upwardly facing edge connector 144.

Figure 4:
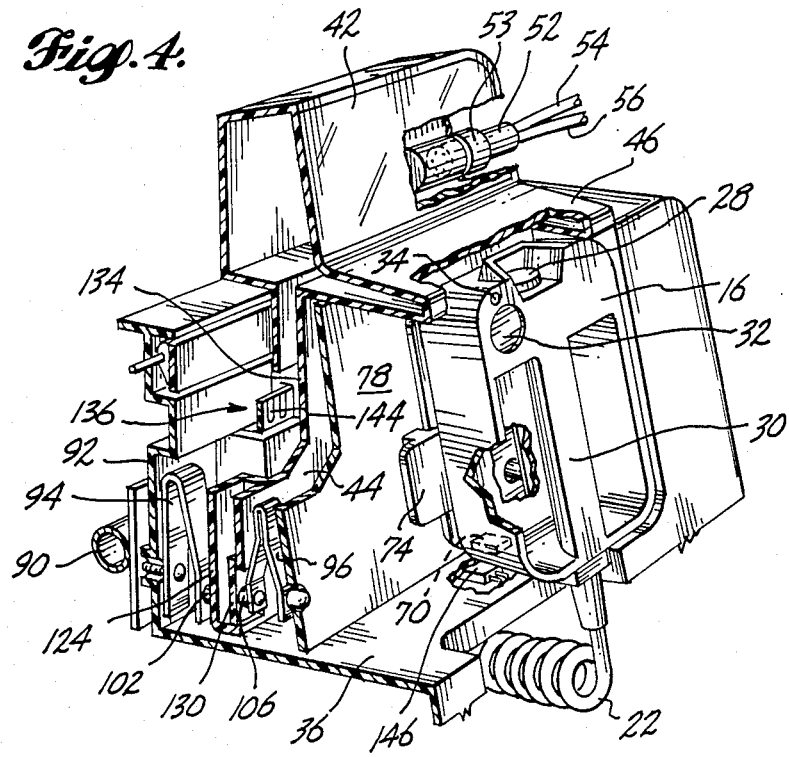
FIG. 4 is a partially cut away perspective view showing the accessory cassette mounted to the defibrillator.

FIG. 4 illustrates the defibrillator and cassette of the present invention with tongue 44 of the cassette fully inserted into cavity 136. As indicated, the lower portion of tongue 44 is inserted between conductors 94 and 96, such that the electrical contact between contacts 102 and 106 is broken. Contact 106 now makes electrical contact to contact 130 of tongue 44. Contact 102 makes contact with lower rear surface 124 of tongue 44. The lower rear surface is fabricated from an insulating material, and as result test load 90 is now electrically isolated from the remainder of the defibrillator. In the fully inserted position shown in FIG. 4, edge connector 144 is inserted into edge connector socket 134, thereby making appropriate electrical connections between cassette 40 and defibrillator 10.

FIG. 4 also illustrates reed switch 146 positioned immediately below lower wall 36 of recess 18. When paddle electrode 16 is stowed in recess 18, the presence of magnet 70 is sensed by reed switch 146, resulting in an electrical signal that may be used by the defibrillator, as described below, to determine that the paddle electrode has been stowed. A similar reed switch (not shown) is positioned beneath the left hand side of lower wall 36 and is used for sensing the presence of paddle electrode 14.

Figure 5:
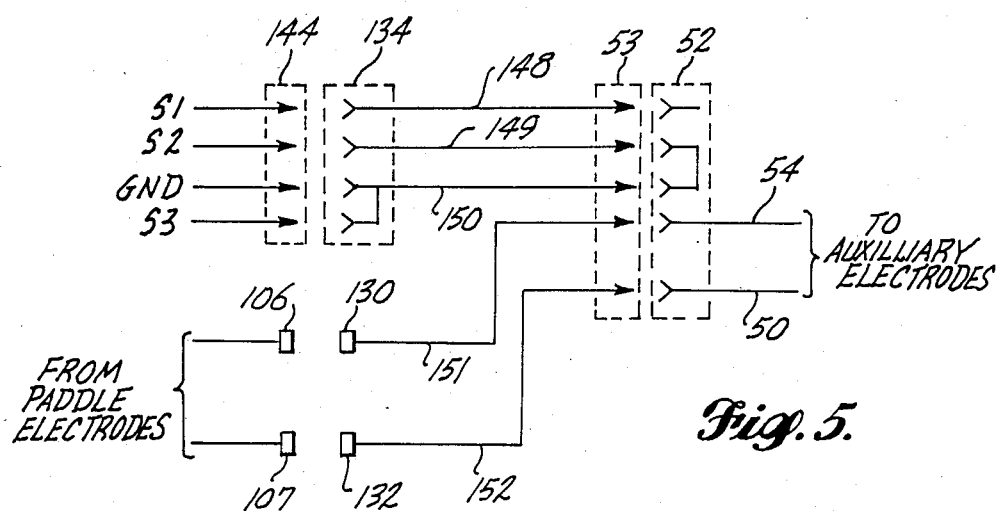
FIG. 5 is an electrical diagram of one embodiment of the accessory cassette.

FIG. 5 illustrates the electrical connections made through cassette 40. Edge connector 144 of defibrillator 10 includes four lines, sense lines S1, S2 and S3 and ground line GND. When cassette 40 is inserted into defibrillator 10, edge connector 144 is connected to edge connector socket 134 in the cassette. Edge connector socket 134 grounds sense line S3, thereby signaling the defibrillator of the presence of cassette 40. Sense lines S1 and S2 and ground line GND are conducted to connector 53 by lines 148–150 respectively. As described above, when the cassette is inserted into the defibrillator, electrical contact is established between contact 106 of conductor 96 and contact 130 in the cassette. A similar electrical contact is made between contact 107 (not shown in FIGS. 1–4) and contact 132 of the cassette. Contacts 130 and 132 are connected to connector 53 by lines 151 and 152.

To use an accessory electrode set, connector 52 of the electrode set is plugged into connector 53 of the cassette. Connector 52 may ground either or both of sense lines S1 and S2, thereby providing information to the defibrillator concerning the nature of the electrode set attached to the cassette. In the embodiment illustrated in FIG. 5, connector 52 grounds sense line S2. Connector 52 also establishes contact between lines 151 and 152 and cables 54 and 56 respectively, to thereby complete the connection between the paddle electrodes and the accessory electrode set.

The information provided by the grounding of sense lines S1 and/or S2 may be used by the defibrillator to limit the energy that may be selected by the operator. For example, the defibrillator may limit energy selection to 50 joules for internal electrodes and 360 joules for disposable electrodes. The defibrillator may also include logic that will block all discharges when the paddle electrodes have been stowed and sense line S3 has been grounded, unless one of sense lines S1 and S2 has also been grounded, indicating the presence of an accessory electrode set. The stowing of the paddle electrodes is sensed through the magnetic reed switches described above.

Defibrillation through accessory paddles is always accomplished by means of discharge switches 24 and 28 in paddle electrodes 14 and 16 when the paddle electrodes are stowed in recess 18. Discharge into the test load is also accomplished by depressing discharge switches 24 and 28 with the paddle electrodes stowed. Guard 46 of cassette 40 is therefore provided to prevent accidental discharge of the defibrillator through accessory electrodes when a test load discharge is intended. When cassette 40 is inserted into defibrillator 10, guard 46 is positioned over discharge switches 24 and 28. With the guard so positioned, access to the discharge switches (with the paddle electrodes stowed) is partially blocked. More operator attention is therefore required in order to discharge the defibrillator under such conditions, and the possibility of accidental discharge through accessory electrodes is therefore minimized.

The cassette feature of the defibrillator may be used to connect other devices to the defibrillator. For example, cassette 40 could comprise a pacemaker that was electrically connected to the defibrillator via edge connector socket 134 and edge connector 144. In this embodiment, contacts 130 and 132 would not be present, and the tongue of the cassette would simply break the connection between the paddle electrodes and the test load. Electrode set 50 would then comprise an appropriate pacing electrode set, and guard 46 would be unnecessary and could be eliminated. In such an embodiment, electronic displays and controls required for pacing logic and pacing current generation would be principally contained within the cassette. However, the cassette would be supported by power supplies and electrical interfaces provided by the defibrillator. More particularly, the interface represented by edge connector socket 134 and edge connector 144 could be adapted to provide the following typical output signals from the cassette to the defibrillator; demand mode selected; nondemand mode selected; audio signal; eyeclose signal; pacing activated; electrodes off; pace rate and pace current. Input signals from the defibrillator to the cassette could include an ECG valid signal and a sync pulse for use in demand pacing.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. A defibrillator, comprising:
a body including a source of defibrillation energy;
a pair of electrodes, each electrode including an electrically conductive electrode element having a generally planar surface for application to a patient and through which a defibrillation shock may be delivered to the patient;
mounting means for mounting the electrodes to the body;
means for electrically connecting the source of defibrillation energy to the electrode elements;
an adapter for connecting an accessory electrode set to the defibrillator, the adapter comprising first and second contact sets and means for electrically connecting the first and second contact sets, the second contact set being adapted to make electrical connection to the accessory electrode set;
means for mounting the adapter to the body; and
contact means for electrically connecting the electrode elements to the first contact set of the adapter when both the electrodes and the adapter are mounted to the body, the contact means being mounted in the body and directly contacting the electrode elements when the electrodes are mounted to the body.

2. The defibrillator of claim 1, further comprising a test load mounted in the body, and wherein the contact means includes means for electrically connecting the test load to the electrode elements when the adapter is not mounted to the body and the electrodes are mounted to the body, and for breaking the electrical connection between the test load and the electrode elements when the adapter is mounted to the body.

3. The defibrillator of claim 1, wherein for each electrode and associated electrode element, the contact means comprises a first conductive element that includes first and second contacts, the first contact being positioned such that the first contact contacts the electrode element when the electrode is mounted to the body, and a second conductive element that is electrically connected to the test load and that includes a third contact, the first and second conductive elements including means for resiliently urging the second and third contacts, into physical and electrical contact with one another, the first and second conductive elements being positioned such that when the adapter is mounted to the body, the adapter is interposed between the second and third contacts and breaks the electrical connection therebetween.

4. The defibrillator of claim 3, wherein the first contact set of the adapter is positioned to make physical and electrical contact with the second contacts when the adapter is interposed between the second and third contacts.

* * * * *

UNITED STATES PATENT AND TRADEMARK OFFICE
CERTIFICATE OF CORRECTION

PATENT NO. : 4,628,935

DATED : December 16, 1986

INVENTOR(S) : Paul W. Jones et al.

It is certified that error appears in the above-identified patent and that said Letters Patent is hereby corrected as shown below:

Column 6, line 46, "1" should be --2--

Signed and Sealed this

Twenty-fourth Day of March, 1987

*Attest:*

DONALD J. QUIGG

*Attesting Officer*      *Commissioner of Patents and Trademarks*